United States Patent [19]

Behl et al.

[11] Patent Number: 4,596,147
[45] Date of Patent: Jun. 24, 1986

[54] ELECTRODYNAMIC TRANSDUCER HEAD

[75] Inventors: Ekkehard Behl, Alzenau-Hörstein; Gerhard Hüschelrath, Laufach-Frohnhofen; Ewald Kowol, Wehrheim, all of Fed. Rep. of Germany

[73] Assignee: Nukem GmbH, Hanau, Fed. Rep. of Germany

[21] Appl. No.: 690,623

[22] Filed: Jan. 11, 1985

[30] Foreign Application Priority Data

Jan. 13, 1984 [DE] Fed. Rep. of Germany ....... 3401072

[51] Int. Cl.[4] ........................................... G01N 29/04
[52] U.S. Cl. .................................................... 73/643
[58] Field of Search .................. 73/643, 661; 324/222, 324/225, 226

[56] References Cited

U.S. PATENT DOCUMENTS 3,512,402  5/1970  Foster .................................... 73/661
4,348,903  9/1982  Sato et al. .............................. 73/643
4,450,725  5/1984  Yamaguchi et al. .................... 73/643
4,480,477  11/1984 Hüschelrath et al. .................. 73/643

FOREIGN PATENT DOCUMENTS 2006433  5/1979  United Kingdom ................... 73/643

Primary Examiner—Stephen A. Kreitman
Attorney, Agent, or Firm—Cushman, Darby & Cushman

[57] ABSTRACT

An electrodynamic transducer head for the non-destructive ultrasonic testing of workpieces (12) comprises an electromagnet having a magnet yoke with an external pole shoe and an internal pole shoe (10, 14) surrounded by the external pole shoe. Exciting and receiving coils (16, 18) are arranged on these pole shoes. To enable the internal pole shoe (10, 14) to be placed directly on the workpiece (12) moving relative thereto without danger, these pole shoes are provided with a protective cap (20) surrounded by a protective ring (22), the end face of the protective ring (22) turned towards the workpiece (12) projecting beyond that of the protective cap.

13 Claims, 2 Drawing Figures

ELECTRODYNAMIC TRANSDUCER HEAD

FIELD OF THE INVENTION

The invention relates to an electrodynamic transducer head for the non-destructive ultrasonic testing of workpieces, preferably using an electromagnet having a magnet yoke with an external pole shoe and with an internal pole shoe which is surrounded by the external pole shoe and preferably tapers conically towards the workpiece, wherein exciting coils and receiving coils which themselves have a cover, at least on the side facing the workpiece, are arranged in the region of the free end face of the magnet yoke facing the workpiece.

BACKGROUND OF THE INVENTION

An electrodynamic transducer head of this type is disclosed in GB-A-20 06 433. In this case, the electromagnet required consists of two coaxial poles whose end faces directed towards the workpiece to be tested match the geometry of the surface of the workpiece to be tested. An exciting coil and receiving coil, which are covered by a ceramic layer on the workpiece side and by an insulating layer on the magnet pole side, are arranged on the internal pole shoe which also consists of two coaxial portions, on the front face thereof. One of the drawbacks of this design of pole shoes is that feedback from the workpiece to be tested and the resulting eddy currents in the pole shoe prevent the resolution of the test signal from being influenced. Furthermore, it is not possible to place an electrodynamic transducer head of this type in the region of the exciting and receiving coil directly on the workpiece and to take measurements while the electromagnet is rotating and/or while the workpiece is rotating because the surface of the workpiece, which resembles emery paper, would instantly destroy the exciting and receiving coil. In other words, the cover composed of ceramic materials is not resistant to abrasion.

DE-OS 31 23 935 describes an electrodynamic transducer head which also comprises an internal pole of an electromagnet surrounded by an external pole shoe, the internal pole shoe having exciting and receiving coils on its end face and also having radial slits into which transformer plates, insulated if necessary, may be introduced. This arrangement should eliminate feedback from the workpiece into the pole shoe, allowing high resolution of the measured values. However, an electrodynamic transducer head of this type cannot be placed on a workpiece to be tested, in particular on a tube, and cannot be moved relative thereto because this would lead to immediate destruction of the measuring system.

SUMMARY OF THE INVENTION

An object of the present invention is to design an electrodynamic transducer head of the type just described such that the electrodynamic transducer head can be safely placed on a workpiece, in particular on a tube, and such that the electrodynamic transducer and the workpiece can move relative to one another without destroying the exciting and receiving coil.

The object is achieved according to the invention in that the cover is a protective cap which is arranged at a distance from the exciting and receiving coil and is surrounded, at least in part, by a protective ring or sections of a protective ring, the end face of the protective ring turned towards the workpiece projecting beyond that of the protective cap. The end face of the internal pole of the electromagnet, which comprises the exciting and receiving coil of the electrodynamic transducer head, is protected from destruction by a protective cap according to the proposal of the invention, the protective cap preferably being composed of metal with a nitrided surface and having radial slits to prevent the formation of eddy currents. In this arrangement, the protective cap itself is prevented from making direct contact with the surface of a workpiece, preferably in the form of a tube, by a protective ring which receives the cap, which can be called a protective sliding ring and can be composed of solid hard metal of G10 quality. This protective sliding ring is in turn soldered on to a cylindrical element which partially surrounds the internal pole shoe in the head region and can, in turn, be screwed on to a holding ring originating from the side wall of the internal pole shoe.

The protective cap itself, which has the shape of a truncated cone and has a lower encircling edge running parallel to the end face, rests, on the pole shoe side, on a cap holder preferably composed of epoxy resin-bonded cloth which rests on the side wall of the conical head portion of the internal pole shoe. The protective cap is consequently secured between sections of the protective ring and the cap holder, and an O-ring seal can be arranged between the lower side of the protective ring and the encircling edge of the protective cap.

The materal used for the protective cap should be kept thin so that the test results are not adversely affected by arranging the protective cap in front of the exciting and receiving coil. The material for a protective cap having a diameter of about 20 to 30 mm is preferably between 0.3 and 0.5 mm thick, a thickness of 0.4 mm having proven to be particularly desirable. The radial slits in the protective cap should be of a width which is smaller than the thickness of the protective cap material. The width should lie between 0.2 and 0.4 mm, a value of 0.3 mm being of particular interest. Furthermore, the slits should preferably end at a distance from the center of the protective cap such that the stability of the protective cap is not influenced.

BRIEF DESCRIPTION OF THE DRAWINGS

Further details, advantages and features of the invention will be revealed by the embodiment illustrated in the drawings, without this limiting the teaching according to the invention.

DETAILED DESCRIPTION OF THE INVENTION

Figure 1:
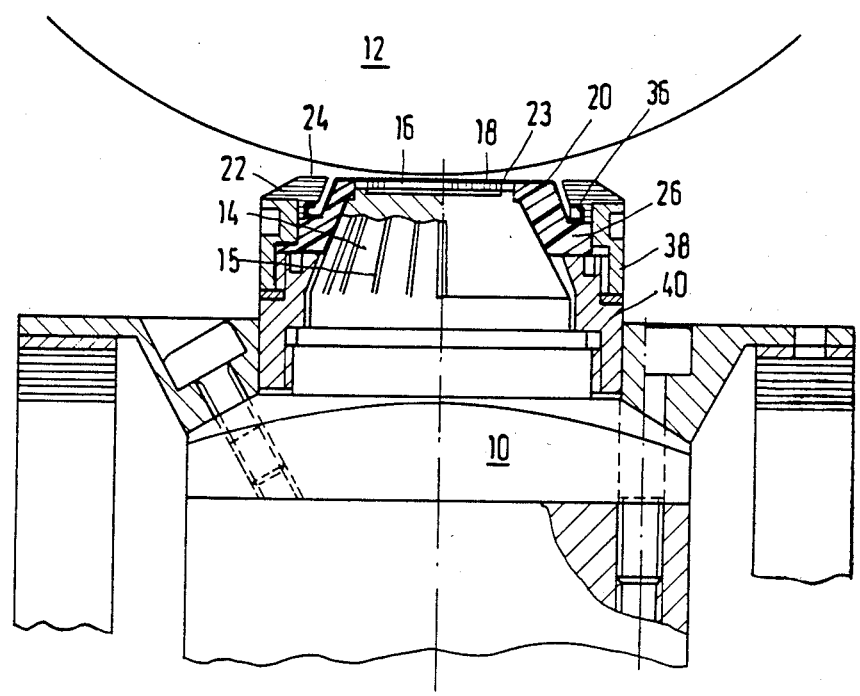
FIG. 1 shows a section of an electrodynamic transducer head.

The electrodynamic transducer head shown in section in FIG. 1 comprises an electromagnet which comprises a magnet yoke with an external pole shoe (not shown) and an internal pole shoe 10 surrounded thereby. The internal pole shoe, which is aligned on a tubular workpiece 12, has an end portion 14 tapering towards the workpiece 12 and having radial slits 15 into which insulated transformer plates (not shown) may be introduced. Appropriate design of the pole shoe head 14 prevents eddy currents from being produced therein as these could distort the test results. Exciting and receiving coils 16 and 18, required for electrodynamic excitation, are located on the end of the pole shoe head 14. (The electrodynamic production of ultrasound in electrically conductive media is based, as known, on the interaction of eddy currents with static magnetic fields, causing movement of particles in the workpiece, i.e. the ultrasonic waves. The necessary magnetic field is preferably produced by an electromagnet with an appropriate pole shoe configuration. Eddy currents are produced in the workpiece, to a depth of penetration dependent on the frequency used, by means of high frequency currents guided through the wires of the exciting coil.).

To enable the probe to be placed directly on the workpiece 12 in the region of the internal pole shoe 10 without the exciting and receiving coils 16 and 18 being damaged by the relative movement between the workpiece 12 and the internal pole shoe 10, it is proposed according to the invention, that the end face of the pole shoe 10 be provided with a protective cap 20 which extends over the entire end face 23. As this protective cap must be of a very thin design to avoid distorting the test signals, the protective cap 20 itself is surrounded by a protective ring 22, the end face 24 of the protective ring 22 turned towards the workpiece 12 projecting beyond the surface of the protective cap 20. Consequently, if a probe having the appropriate cover comes to rest on the workpiece 12, this ensures that the protective cap 20 is not contacted by the workpiece 12. Rather, the protective ring 22 interacts with the surface of the workpiece 12 which frequently bears powdered scale, resembling emery paper. However, as the protective ring 22, which is more appropriately known as a protective sliding ring, is composed of a solid hard metal material, for example of grade G10, this ensures that the protective cap 20 normally remains undamaged.

FIG. 1 also shows that the protective cap 20, composed of a highly abrasion-resistant metal, is supported on a cap holder 26 which, in turn, rests against the side wall of the conical internal pole shoe head 14. The cap holder 26 is preferably composed of an epoxy-resin-bonded cloth mixture. The geometry of the external surface of the cap holder 26 is adapted to the geometry of the protective cap 20 outside the end region of the pole shoe 14. The protective cap 20 preferably has the shape of a truncated cone with its lower encircling edge 34 bent outwards.

Figure 2:
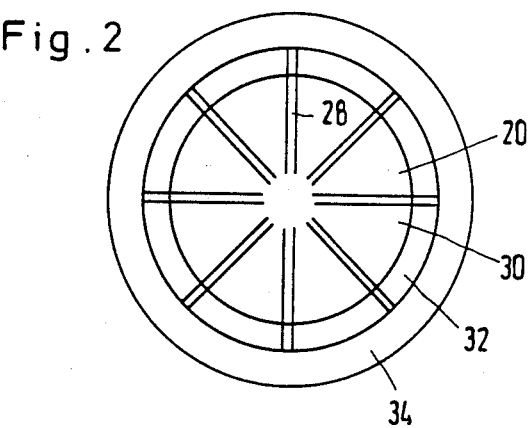
FIG. 2 shows a plan view of a protective cap provided in the transducer head according to FIG. 1.

FIG. 2 shows a plan view of the cap 20 which is preferably composed of steel. The cap 20 has radial slits 28 which are at a distance from the center and ensure that eddy currents cannot be produced in the protective cap 20 composed of metal. It can also be seen that the cap is composed of three portions, namely the end face 30 comprising the slits 28, the side face 32 running obliquely outwards and the encircling edge face 34 with its plane parallel to that of the end face 30. The edge face 34 is thus arranged between the lower side of the protective sliding ring 22 and the cap holder 26, and an O-ring seal 36 can be provided between the edge face 30 and the receiving sliding ring 24. A protective cap 20 of suitable design can have the following dimensions: diameter of end face 30 approximately 21 mm, diameter of lower side in the region of edge face 34 approximately 29 mm, thickness of the material in region of end face 30 approximately 0.4 mm and height of protective cap approximately 4 mm.

The protective sliding ring 22 is soldered on to a cylindrical ring element 38 which, in turn, can be screwed on to a holding ring 40 originating from the surface of the pole shoe 10. The external surface of the cylindrical ring element 38 can be additionally secured by an encircling fixed claw (not shown) which, in turn, is detachably connected to the electromagnet by screw connections.

The pole shoe 10 is able to slide safely along the surface of the workpiece to be tested 12 as a result of covering the pole shoe 10 comprising the exciting and receiving coil 16, 18 in the manner according to the invention. The screen can be very thin in the region of the coils 16, 18 because the protective cap 20 covering the end face 23 of the pole shoe 14 is itself surrounded by a projecting protective sliding ring 22.

We claim:

1. An electrodynamic transducer head for the non-destructive ultrasonic testing of workpieces, preferably using an electromagnet having a magnet yoke with an external pole shoe and with an internal pole shoe which is surrounded by the external pole shoe and preferably tapers conically towards the workpiece, wherein exciting coils and receiving coils which themselves have a cover, at least on the side facing the workpiece, are arranged in the region of the free end face of the magnet yoke facing the workpiece, characterised in that the cover is a protective cap which is arranged at a distance from the exciting and receiving coils and is surrounded, at least in part, by a protective ring or sections of a protective ring, the end face of the protective ring turned towards the workpiece projecting beyond that of the protective cap, said protective cap being comprised of metal having a preferably nitrided surface and comprising radial slits.

2. Transducer head according to claim 1, characterised in that the thickness of the material of the protective cap in the region above the end face of the internal pole shoe lies in the range of from 0.3 to 0.5 mm.

3. Transducer head according to claim 1, characterised in that the protective cap has the shape of a truncated cone, with a lower edge which is bent outwards and runs parallel to the end face, and, outside the end face of the internal pole shoe said protective cap rests on a cap holder which is supported on the internal pole shoe.

4. Transducer head according to claim 3, characterised in that the cap holder is comprised of an epoxy resin-bonded cloth material.

5. Transducer head according to claim 1, characterised in that the protective ring is comprised of a hard metal ring turned towards the workpiece and of a hollow cylindrical element which coaxially surrounds the internal pole shoe and, in turn, laterally surrounds the cap holder.

6. Transducer head according to claim 5, characterised in that the hard metal ring is soldered on to the hollow cylindrical element.

7. Transducer head according to claim 5, characterised in that the hollow cylindrical element is detachably connected to a holding ring originating from the external surface of the internal pole shoe.

8. An electrodynamic transducer head for non-destructive testing of a workpiece by means of ultrasonic waves, comprising:
    a magnet having a magnet yoke with external pole shoes and an inner pole shoe being surrounded by the external pole shoes;
    exciting and receiving cells being arranged in the region of the free end face of said inner pole shoe facing said workpiece; and a cover for said exciting and receiving coils, said cover being provided at least on the side facing said workpiece, being arranged at a distance from said exciting and receiving coils, being made of metal and having radial slits.

9. A transducer head as claimed in claim 8, wherein said cover, at least partially, is received by a protective element having an end face facing said workpiece which projects beyond said cover.

10. A transducer head as claimed in claim 8, wherein the thickness of said cover in said region above the end face of said inner pole shoe ranges between 0.3 and 0.5 mm.

11. A transducer head as claimed in claim 8, wherein said cover having a nitrided surface.

12. A transducer head as claimed in claim 8 wherein said cover has the shape of a truncated cone having a lower edge bent outwards and running parallel to the end face and further comprising a holder supported by said inner pole shoe, said cover outside the end face of said inner pole shoe rests on said holder.

13. A transducer head as claimed in claim 12, wherein said holder is comprised of a laminate plastic-epoxies material.

* * * * *